United States Patent
Kilian et al.

(10) Patent No.: US 9,949,478 B2
(45) Date of Patent: Apr. 24, 2018

(54) HERBICIDAL COMBINATION WITH HERBICIDAL ACTIVE FATTY ACIDS AND AN ALS-INHIBITOR

(71) Applicant: BAYER CROPSCIENCE AKTIENGESELLSCHAFT, Monheim am Rhein (DE)

(72) Inventors: Michael Kilian, Leverkusen (DE); Christian Marienhagen, Langenfeld (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/897,969

(22) PCT Filed: Jul. 8, 2014

(86) PCT No.: PCT/EP2014/064504
§ 371 (c)(1),
(2) Date: Dec. 11, 2015

(87) PCT Pub. No.: WO2015/004087
PCT Pub. Date: Jan. 15, 2015

(65) Prior Publication Data
US 2016/0143278 A1    May 26, 2016

(30) Foreign Application Priority Data
Jul. 12, 2013    (EP) ..................... 13176240

(51) Int. Cl.
*A01N 37/02*    (2006.01)
*A01N 47/36*    (2006.01)
*A01N 47/38*    (2006.01)
*A01N 47/30*    (2006.01)

(52) U.S. Cl.
CPC ............. *A01N 37/02* (2013.01); *A01N 47/30* (2013.01); *A01N 47/36* (2013.01); *A01N 47/38* (2013.01)

(58) Field of Classification Search
CPC ........ A01N 37/02; A01N 47/30; A01N 47/38; A01N 47/36
See application file for complete search history.

(56) References Cited

U.S. PATENT DOCUMENTS 5,106,410 A    4/1992    Puritch et al.
6,503,869 B1    1/2003    Beste et al.

FOREIGN PATENT DOCUMENTS

| CN | 102217626 A | 10/2011 | |
|----|-------------|---------|---|
| EP | 0494386 A1 | 7/1992 | |
| WO | 2008142391 A1 | 11/2008 | |
| WO | WO 2014016229 A1 * | 1/2014 | ............. A01N 37/02 |

OTHER PUBLICATIONS

Equip Corn Herbicide Product Sheet, Dec. 2004, Bayer CorpScience, pp. 1-11.*
Lenthe et al., EP12177824.5, Certified priority document, Priority Document for WO 2014/016229, Jul. 25, 2012, 25 pages.*
International Search Report from corresponding PCT/EP2014/064503, dated Sep. 16, 2014.
International Search Report from PCT/EP2014/064504, dated Sep. 24, 2014.
Database WPI Week 201241, Thomson Scientific, London, GB, AN 2011-P33732, XP002712978.
European Search Report from corresponding EP 13 17 6240, dated Sep. 16, 2013.

* cited by examiner

*Primary Examiner* — John Pak
*Assistant Examiner* — Andriae M Holt
(74) *Attorney, Agent, or Firm* — McBee Moore Woodward & Vanik IP, LLC

(57) ABSTRACT

The present invention relates to a herbicide combination comprising at least two α-monocarboxyl fatty acids having, independently of one another, a hydrocarbon chain having 8 to 10 carbon atoms, and at least one ALS inhibitor.

13 Claims, No Drawings

HERBICIDAL COMBINATION WITH HERBICIDAL ACTIVE FATTY ACIDS AND AN ALS-INHIBITOR

CROSS REFERENCE TO RELATED APPLICATIONS

This application is a § 371 National Stage Application of PCT/EP2014/064504, filed 8 Jul. 2014, which claims priority to EP 13176240.3, filed 12 Jul. 2013.

BACKGROUND

Field of the Invention

The present invention is in the technical field of crop protection compositions which can be employed against unwanted vegetation, for example by the post-emergence method in sown and/or planted crop plants, in fruit plantations (plantation crops), on non-crop areas (e.g. squares of residential areas or industrial sites, rail tracks) and on lawns. In addition to the single application, sequential applications are also possible.

Description of Related Art

The present invention relates to a herbicide combination and its application for controlling unwanted vegetation, in particular a herbicide combination comprising at least two herbicidally active fatty acids and at least one ALS inhibitor.

Herbicidally active fatty acids are known from the prior art.

A compound from the substance class of the ALS inhibitors inhibits the enyzme acetolactate synthase (ALS) which is responsible for the biosynthesis of branched amino acids such as L-valine, L-leucine and L-isoleucine. Therefore, this substance class—in addition to other substance classes—is, according to its mechanism of action, assigned to the group of the ALS (acetolactate synthase) inhibitors (see also http://www.hracglobal.com/Portals/5/moaposter.pdf). The ALS inhibitors include, for example, the sulfonylureas (see also, for example, "The Pesticide Manual" $15^{th}$, Edition, British Crop Protection Council 2011). These herbicides are in particular frequently applied on fields cultivated with soybeans and cereals. Uptake of these herbicides is via the roots and leaves.

The herbicidal activity of such herbicides against harmful plants (broad-leaved weeds, weed grasses, cyperaceae; hereinbelow together also referred to as "weed") is already on a high level, but generally depends on the application rate, the respective preparation form, the respective harmful plants to be controlled or the spectrum of harmful plants, the climatic and soil conditions, etc. Further criteria in this context are duration of action, or the breakdown rate, of the herbicide, the general crop plant compatibility and speed of action (more rapid onset of action), the activity spectrum and behavior toward follower crops (replanting problems) or the general flexibility of application (control of weeds in their various growth stages). If appropriate, changes in the susceptibility of harmful plants, which may occur on prolonged use of the herbicides or in limited geographical regions (control of tolerant or resistant weed species), may also have to be taken into account. The compensation of losses in action in the case of individual plants by increasing the application rates of the herbicides is only possible to a certain degree, for example because such a procedure reduces the selectivity of the herbicides or because the action is not improved, even when applying higher rates.

Thus, there is frequently a need for targeted synergistic activity against specific weed species, weed control with better overall selectivity, generally lower amounts of active compounds used for equally good control results and for a reduced active compound input into the environment to avoid, for example, leaching and carry-over effects. There is also a need for developing one-shot applications to avoid labor-intensive multiple applications, and also to develop systems for controlling the rate of action, where, in addition to an initial rapid control of weeds, there is also a slow, residual control.

A possible solution to the problems mentioned above may be to provide herbicide combinations, that is mixtures of a plurality of herbicides and/or other components from the group of the agrochemically active compounds of a different type and of formulation auxiliaries and additives customary in crop protection which contribute the desired additional properties. However, in the combined use of a plurality of active compounds, there are frequently phenomena of chemical, physical or biological incompatibility, for example lack of stability in a joint formulation, decomposition of an active compound or antagonism in the biological activity of the active compounds. For these reasons, potentially suitable combinations have to be selected in a targeted manner and tested experimentally for their suitability, it not being possible to safely discount a priori negative or positive results.

SUMMARY

It was the object of the present invention to provide crop protection compositions as alternatives to the prior art, or as an improvement thereof.

Surprisingly it has now been found that this object can be achieved by the combination of at least two herbicidally active fatty acids in a certain mixing ratio and at least one ALS inhibitor which interact in a particularly favorable manner; for example when they are employed for controlling unwanted vegetation in sown and/or planted crop plants, greens/lawns, in fruit plantations (plantation crops) or on non-crop areas (e.g. squares of residential areas or industrial sites, rail tracks. Surprisingly, the activity of the combinations according to the invention of a plurality of active compounds, when used against weeds, is higher than the activities of the individual components. A true synergistic effect which could not have been predicted therefore exists, not just a complementation of action (additive effect).

Herbicidally active fatty acids which can be used according to the invention comprise at least two α-monocarboxyl fatty acids which, independently of one another, contain hydrocarbon chains having 8 to 10 carbon atoms and are in a ratio of between 65:35 and 40:60 to one another (preferably in a ratio of 60 to 40). An example of a fatty acid component which is preferred according to the invention is Palmera A5608® (67762-36-1) from Croda. The fatty acids are preferably selected from the group consisting of caprylic acid, pelargonic acid, capric acid, undecanoic acid and lauric acid. According to the invention, the herbicidally active fatty acids preferably comprise at least (preferably exactly) two α-monocarboxyl fatty acids, where one α-monocarboxyl fatty acid has hydrocarbon chains having 8 carbon atoms and the other α-monocarboxyl fatty acid has hydrocarbon chains having 10 carbon atoms, and which are in a ratio of between 65:35 and 40:60 to one another (preferably in a ratio of 60 to 40).

The fatty acid components listed above are examples of the fatty acid mixtures currently preferred. It is clear that the ratios of the various constituents of these fatty acids and mixtures can be changed or that other combinations of fatty acids having 8 to 10 carbon atoms can be used to achieve the same or even better results. Preferably, the active constituents (active compounds) are a mixture of unhydrolyzed fatty acids.

The ALS inhibitor employed can be a compound selected from the group consisting of the imidazolinones, pyrimidinyloxypyridinecarboxylic acid derivatives, pyrimidyloxybenzoic acid derivatives, sulfonamides or sulfonylureas. The ALS inhibitor employed is preferably a compound selected from the group consisting of herbicidally active sulfonylureas and sulfonamides. The herbicidally active sulfonylurea employed is preferably a compound selected from the group consisting of amidosulfuron, azimsulfuron, cyclosulfamuron, bensulfuron-methyl, chlorimuron-ethyl, chlorsulfuron, cinosulfuron, cyclosulfuron, ethametsulfuron-methyl, ethoxysulfuron, flazasulfuron, flucetosulfuron, flupyrsulfuron, foramsulfuron, halosulfuron-methyl, imazosulfuron, iodosulfuron-methyl (in particular the sodium salt), isosulfuron-methyl, mesosulfuron-methyl, metsulfuron-methyl, nicosulfuron, oxasulfuron, orthosulfamuron, primisulfuron-methyl, prosulfuron, pyrazosulfuron-ethyl, propyrisulfuron, rimsulfuron, sulfometuron-methyl, sulfosulfuron, thifensulfuron-methyl, triasulfuron, tribenuron-methyl, trifloxysulfuron-sodium, triflusulfuron-methyl, tritosulfuron and their salts. The herbicidally active sulfonamide employed is preferably a compound selected from the group consisting of thiencarbazone-methyl triazolopyrimidinesulfonamides, sulfonylaminocarbonyltriazolinones and their salts.

Herbicidally active sulfonylureas which are preferred according to the invention are selected from the group consisting of iodosulfuron-methyl (IUPAC name: 4-iodo-2-[(4-methoxy-6-methyl-1,3,5-triazin-2-yl)carbamoylsulfamoyl]benzoate, sodium salt), foramsulfuron (IUPAC name: 1-(4,6-dimethoxypyrimidin-2yl)-3-(2-dimethylcarbamoyl-5-formamidophenylsulfonyl)urea, mesosulfuron-methyl (IUPAC name: methyl 2-[(4,6-dimethoxypyrimidin-2-ylcarbamoyl)sulfamoyl]-a-(methanesulfonamido)-p-toluate), flazasulfuron (IUPAC name: 1-(4,6-dimethoxypyrimidin-2-yl)-3-(3-trifluoromethyl-2-pyridylsulfonyl)urea), amidosulfuron (IUPAC: 3-(4,6-dimethoxypyrimidin-2-yl)-1-(N-methyl-N-methylsulfonylaminosulfonyl)urea), ethoxysulfuron (IUPAC name: 2-ethoxyphenyl[(4,6-dimethoxypyrimidin-2-yl)carbamoyl]sulfamate). A herbicidally active sulfonamide which is preferred according to the invention is thiencarbazone methyl (IUPAC name: methyl 4-[(4,5-dihydro-3-methoxy-4-methyl-5-oxo-1H-1,2,4-triazol-1yl)carbonylsulfamoyl]-5-methylthiophene-3-carboxylate).

Particular preference is given to using iodosulfuron-methyl (especially the sodium salt) and/or foramsulfuron and especially to using iodosulfuron-methyl (especially the sodium salt) and foramsulfuron together. The invention also encompasses combinations of ALS inhibitors and especially of two or more sulfonylureas having complementary activity spectra.

Hereinbelow, the terms "herbicide(s)", "individual herbicide(s)", "compound(s)" or "active compound(s)" are also used synonymously for the term "components(s)" in the context.

Additionally, the herbicide combination according to the invention may comprise further components, for example agrochemically active compounds of a different type and/or the formulation auxiliaries and/or additives customary in crop protection, or may be used together with these. Hereinbelow, the use of the term "herbicide combination(s)" or "combination(s)" also includes the "herbicidal compositions" formed in this manner.

DETAILED DESCRIPTION OF A PREFERRED EMBODIMENT

In a preferred embodiment, the herbicide combination according to the invention comprises an effective amount of at least two herbicidally active fatty acids and at least one ALS inhibitor and/or has synergistic activities. The synergistic actions can be observed, for example, in the case of joint application, for example as a ready-to-use formulation, co-formulation or as a tank mix; however, they can also be observed when the active compounds are applied at different times (splitting) (packed, for example, as combipack or monodoses). It is also possible to apply the herbicides or the herbicide combination in a plurality of portions (sequential application), for example post-emergence applications or early post-emergence applications followed by medium or late post-emergence applications. Here, the joint application of the herbicide combination according to the invention is preferred. Substances attracting protons (fatty acids, among others) destabilize sulfonylureas. This means that sulfonylureas and fatty acids can not, or only with great difficulties, be formulated together as a solo formulation, which requires certain demands with regard to the packaging of the crop protection composition to be met. If fatty acids and sulfonylurea are, as in the tests, to be applied as tank mixes, it has to be ensured that the spray liquor is applied relatively quickly after preparation.

The synergistic effects permit a reduction of the application rates of the individual herbicides, a higher and/or longer efficacy at the same application rate, the control of species which were as yet uncontrolled (gaps), control of species which are tolerant or resistant to individual herbicides or to a number of herbicides, an extension of the period of application and/or a reduction in the number of individual applications required and—as a result for the user—weed control systems which are more advantageous economically and ecologically.

In the herbicide combination according to the invention, the application rate of the herbicidally active fatty acids may vary within a wide range; for example, the application rate should be at least 2500 g of AS/ha (hereinbelow, AS/ha means "active substance per hectare"=based on 100% active compound), but preferably between 2500 and 30000 g of AS/ha, more preferably between 10000 and 30000 g of AS/ha and most preferably between 20000-30000 g of AS/ha.

In the herbicide combination according to the invention, the application rate of the herbicidally active ALS inhibitor may vary within a wide range, for example between 1 g and 200 g of AS/ha, with a relatively wide spectrum of harmful plants being controlled.

If foramsulfuron is used, the application rate is preferably in a range of 15-60 g of AS/ha and even more preferably between 30-60 and particularly preferably between 30-45 g of AS/ha.

If iodosulfuron is used, the application rate is preferably in a range of 1 and 10 g of AS/ha and even more preferably between 1-5 g of AS/ha.

If mesosulfuron is used, the application rate is preferably in a range of 7.5 and 30 g of AS/ha.

If thiencarbazone is used, the application rate is preferably in a range of 10 and 30 g of AS/ha.

If flazasulfuron is used, the application rate is preferably in a range of 10 and 50 g of AS/ha.

If amidosulfuron is used, the application rate is preferably in a range of 30 and 60 g of AS/ha.

If ethoxysulfuron is used, the application rate is preferably in a range of 60 and 200 g of AS/ha.

Ranges of suitable ratios of the herbicidally active fatty acids and the herbicidally active ALS inhibitor can be found, for example, by looking at the application rates mentioned for the individual compounds. In the combination according to the invention, the application rates can generally be reduced. Preferred mixing ratios of the combined herbicidally active fatty acids (hereinbelow referred to as component "A" or just as "A") and the herbicidally active ALS inhibitor (hereinbelow referred to as component "B" or just as "B") described according to the invention in the combination according to the invention are characterized by the following weight ratios:

The weight ratio (A):(B) of the components (A) and (B) is generally in the range of from 30000:1 to 12.5:1, preferably 30000:1 to 50:1.

The following weight ratios apply to the preferred combinations of fatty acids plus ALS inhibitor.

When using fatty acids and foramsulfuron, the weight ratio is preferably in the range from 2000:1 to 167:1 and even more preferably in the range from 1000:1 to 333:1 and particularly preferably in the range from 1000:1 to 444:1.

When using fatty acids and iodosulfuron, the weight ratio is preferably in a range from 30000:1 to 1000:1 and even more preferably in the range from 30000:1 to 4000:1.

When using fatty acids and mesosulfuron, the weight ratio is preferably in a range from 4000:1 to 333:1.

When using fatty acids and thiencarbazone, the weight ratio is preferably in a range from 3000:1 to 333:1.

When using fatty acids and flazasulfuron, the weight ratio is preferably in a range from 3000:1 to 200:1.

When using fatty acids and amidosulfuron, the weight ratio is preferably in a range from 1000:1 to 167:1.

When using fatty acids and ethoxysulfuron, the weight ratio is preferably in a range from 500:1 to 50:1.

Preference is given to herbicide combinations which, in addition to the combination according to the invention, also comprise one or more further agrochemically active compounds which also act as a selective herbicide. Particular preference is given to using the combination of at least two herbicidally active fatty acids in a certain mixing ratio and of at least two ALS inhibitors, preferably two herbicidally active sulfonylureas and in particular both foramsulfuron and iodosulfuron.

In the particularly preferred combination of herbicidally active fatty acids with two herbicidally active sulfonylureas in particular the use of foramsulfuron and iodosulfuron-methyl (in particular the sodium salt).

In the particularly preferred combination of herbicidally active fatty acids with foramsulfuron and iodosulfuron-methyl (especially the sodium salt), 15-60 parts by weight of the active compound foramsulfuron and 2500-30000 (preferably 10000-30000, particularly preferably 10000-15000) parts by weight of the herbicidally active fatty acids are present per 1 (one) part by weight of iodosulfuron-methyl. Surprisingly, it has also been found in particular that even small amounts of the herbicidally active fatty acids (10000 g-15000 g of AS/ha) together with foramsulfuron and iodosulfuron-methyl have synergistic effects.

The herbicide combination according to the invention may furthermore comprise, as additional further components, various agrochemically active compounds, for example from the group of the safeners, fungicides, insecticides, acaricides, nematicides, bird repellants, soil structure improvers, plant nutrients (fertilizers), and herbicides and plant growth regulators which differ structurally from the herbicidally active compounds employed in accordance with the invention, or from the group of the formulation auxiliaries and additives customary in crop protection.

The active compound combinations according to the invention have very good herbicidal properties and can be used for controlling weeds. Here, weeds are understood to mean all plants which grow at sites where they are unwanted.

The active compound combinations according to the invention can be used, for example, in connection with the following plants:

Dicotyledonous weeds of the genera: *Cassia, Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Sphenoclea, Taraxacum, Plantago, Epilobium, Rubus, Achillea, Rumex, Lotus, Bettis.*

Monocotyledonous weeds of the genera: *Echinochloa, Eriochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Dactyloctenium, Agrostis, Alopecurus, Apera, Aegilops, Phalaris.*

Mosses and algae

If the active compounds are applied post-emergence to the green parts of the plants, growth likewise stops drastically a very short time after the treatment, and the weed plants remain at the growth stage of the point of time of application, or they die completely after a certain time, so that in this manner weed infestation is eliminated very early and in a sustained manner.

Preferably, the active compound combinations according to the invention can be used as total herbicides for controlling weeds, for example in particular on non-crop areas such as paths, squares and also under trees and shrubs, rail tracks etc. The active compound combinations according to the invention are distinguished by an action which has a particularly quick onset and lasts for a long time.

The herbicide combination according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components. It is also possible to use the herbicides or the herbicide combination in a plurality of portions (sequential application), for example by the post-emergence method or early post-emergence applications followed by medium or late post-emergence applications. Preference is given to the joint use of the active compounds in the respective combination.

Substances attracting protons (fatty acids, among others) destabilize sulfonylureas. This means that sulfonylureas and fatty acids cannot, or only with great difficulties, be formulated together as a solo formulation, which requires certain demands with regard to the packaging of the crop protection composition to be met. If fatty acid and sulfonylurea are, as in the tests, to be applied as tank mixes, it has to be ensured that the spray liquor is applied relatively quickly after preparation. A preferred variant of the invention relates to processes for controlling weeds where component (A) and component (B) of the herbicide combination according to the invention are mixed only shortly before application onto the weeds and/or their habitat. According to the invention, "shortly before application" means that component (A) and component (B) are mixed preferably less than 6 hours, more preferably less than 3 hours and even more preferably less than 1 hour before application onto the weeds and/or their habitat.

Other than that, the at least two herbicidally active fatty acids in a certain mixing ratio and the at least one ALS inhibitor employed in accordance with the invention can be converted jointly or separately into customary formulations, such as solutions, emulsions, suspensions, powders, foams, pastes, granules, aerosols, natural and synthetic materials impregnated with active compound and microencapsulations in polymeric materials. The formulations may comprise the customary auxiliaries and additives.

These formulations are produced in a known manner, for example by mixing the active compounds with extenders, i.e. liquid solvents, pressurized liquefied gases and/or solid carriers, optionally with use of surfactants, i.e. emulsifiers and/or dispersants and/or foam formers.

If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and the ethers and esters thereof, ketones such as acetone, methyl ethyl ketone, methyl isobutyl ketone or cyclohexanone, strongly polar solvents such as dimethylformamide or dimethyl sulfoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, corn cobs and tobacco stalks; useful emulsifiers and/or foam formers include: for example nonionic and anionic emulsifiers, such as polyoxyethylene fatty acid esters, polyoxyethylene fatty alcohol ethers, e.g. alkylaryl polyglycol ethers, alkylsulfonates, alkylsulfates, arylsulfonates and protein hydrolyzates; useful dispersants include: for example lignosulfite waste liquors and methylcellulose.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian blue, and organic colorants such as alizarin colorants, azo colorants and metal phthalocyanine colorants, and trace nutrients such as salts of iron, manganese, boron, copper, cobalt, molybdenum and zinc.

In general, the formulations comprise between 0.1 and 95% by weight of active compound, preferably between 0.2 and 90% by weight.

The herbicide combination according to the invention can be used as such, in the form of its formulations or in the use forms prepared therefrom by further dilution, such as ready-to-use solutions, suspensions, emulsions, powders, pastes and granules. Application is accomplished in a customary manner, for example by watering, spraying, atomizing or broadcasting.

The active compound combinations according to the invention are generally applied in the form of finished formulations. However, the active compounds contained in the active compound combinations can, as individual formulations, also be mixed during use, i.e. be applied in the form of tank mixes.

The good herbicidal action of the novel active compound combinations can be seen from the examples which follow. While the individual active compounds show weaknesses in their herbicidal action, all combinations show a very good action on weeds which exceeds a simple sum of actions.

A synergistic effect in herbicides is always present when the herbicidal action of the active compound combination exceeds the action of the active compounds when applied individually.

The expected activity of a given combination of two or three herbicides can be calculated as follows (cf. COLBY, S. R.: "Calculating synergistic and antagonistic responses of herbicide combinations", Weeds 15, pages 20-22, 1967):

If X=% damage by herbicide (A) at an application rate of m g/ha,
Y=% damage by herbicide (B) at an application rate of n g/ha,
Z=% damage by herbicide (C) at an application rate of r kg/ha,
E1=the expected damage by herbicides (A) and (B) at application rates of m and n kg/ha and,
E2=the expected damage by herbicides (A) and (B) and (C) at application rates of m and n and r kg/ha,
then for a combination:

$$E1 = X + Y - \frac{X \times Y}{100}$$

and for a combination of 3 active compounds:

$$E2 = X + Y + Z - \frac{(X \times Y + X \times Z + Y \times Z)}{100} + \frac{X \times Y \times Z}{10000}$$

If the actual damage exceeds the calculated value, the activity of the combination is superadditive, i.e. it shows a synergistic effect. In this case, the damage actually observed must exceed the values calculated using the above formulae for the expected damages E1 and E2.

The invention is illustrated by the examples below.
Use examples:
The following formulations of the active compounds involved were used:
fatty acids 120 EC (fatty acid mixture of two fatty acids having hydrocarbon chains of 8 and 10 carbon atoms in a ratio of 60 to 40; for the preparation see EP application number 12177824.5; title: "Emulsifiable Concentrate Formulation with Herbicidal Active Fatty Acids); application date: Jul. 25, 2012).

foramsulfuron 50 WG (water dispersible granule) standard granule formulation without adjuvants
iodosulfuron 10 WG (water dispersible granule) (commercial formulation Destiny, approved inter alia in Australia—Bayer CropScience)
mesosulfuron 75 WG (water dispersible granule) standard granule formulation without adjuvants
thiencarbazone 70 WG (water dispersible granule) standard granule formulation without adjuvants
flazasulfuron 25 WG (water dispersible granule) (commercial formulation Chikara, approved inter alia in Germany—product licence holder ISK Biosciences)
amidosulfuron 75 WG (water dispersible granule) (commercial formulation Hoestar, approved inter alia in Germany—Bayer CropScience)
ethoxysulfuron 60 WG (water dispersible granule) (commercial formulation SunRice, approved inter alia in Italy—Bayer CropScience)

The active compound concentrations required for the tests were prepared by dilution with water. The tested active compound combinations were mixed shortly before their biological examination.

Post-emergence Test

Test plants of a height of 5 to 15 cm are sprayed with the preparation of active compound such that the particular amounts of active compound desired are applied per unit area. The concentration of the spray liquor is chosen such that the particular amounts of active compound desired are applied in 1000 l of water/ha. After 34 days (data in Tables 1 to 7) or 48 days (data in Tables 8 to 25), the degree of damage to the plants is rated in % damage in comparison to the development of the untreated control. In the case of all herbicide combinations according to the invention, for most of the test plants synergistic actions are observed (see Tables 1 to 25).

TABLE 1

Table 1: Herbicide combination according to the invention consisting of herbicidally active fatty acids and foramsulfuron.

| Weed | Herbicidally active fatty acids 20000 g of active compound/ha; herbicidal effect [%] | Foramsulfuron 45 g of active compound/ha; herbicidal effect [%] | Herbicidal effect [%] calculated according to Colby | Herbicidal effect [%] found |
|---|---|---|---|---|
| Trifolium repens | 25 | 20 | 40 | 63 |
| Achillea millefolium | 32 | 17 | 44 | 58 |
| Stellaria media | 12 | 18 | 28 | 65 |
| Rumex acetosa | 40 | 11 | 47 | 70 |
| Chenopodium album | 63 | 8 | 66 | 96 |
| Taraxacum officinale | 50 | 55 | 78 | 99 |
| Lotus corniculatus | 7 | 0 | 7 | 62 |
| Plantago lanceolata | 50 | 8 | 54 | 80 |
| Festuca ovina | 17 | 35 | 46 | 96 |
| Plantago major | 37 | 47 | 67 | 78 |
| Ranunculus repens | 18 | 95 | 96 | 97 |
| Bellis perennis | 27 | 13 | 36 | 85 |

TABLE 2

Table 2: Herbicide combination according to the invention consisting of herbicidally active fatty acids and iodosulfuron.

| Weed | Herbicidally active fatty acids 20000 g of active compound/ha; herbicidal effect [%] | Iodosulfuron-methyl sodium salt 1.25 g of active compound/ha; herbicidal effect [%] | Herbicidal effect [%] calculated according to Colby | Herbicidal effect [%] found |
|---|---|---|---|---|
| Trifolium repens | 25 | 10 | 33 | 47 |
| Achillea millefolium | 32 | 5 | 35 | 35 |
| Stellaria media | 12 | 22 | 31 | 40 |
| Rumex acetosa | 40 | 12 | 47 | 62 |
| Chenopodium album | 63 | 13 | 68 | 82 |
| Taraxacum officinale | 50 | 50 | 75 | 99 |
| Lotus corniculatus | 7 | 0 | 7 | 23 |
| Plantago lanceolata | 50 | 3 | 52 | 68 |
| Festuca ovina | 17 | 0 | 17 | 22 |
| Plantago major | 37 | 22 | 51 | 79 |
| Ranunculus repens | 18 | 73 | 78 | 88 |
| Bellis perennis | 27 | 10 | 34 | 63 |

TABLE 3

Table 3: Herbicide combination according to the invention consisting of herbicidally active fatty acids and mesosulfuron.

| Weed | Herbicidally active fatty acids 20000 g of active compound/ha; herbicidal effect [%] | Mesosulfuron-methyl 15 g of active compound/ha; herbicidal effect [%] | Herbicidal effect [%] calculated according to Colby | Herbicidal effect [%] found |
|---|---|---|---|---|
| Trifolium repens | 25 | 2 | 27 | 10 |
| Achillea millefolium | 32 | 4 | 35 | 32 |
| Stellaria media | 12 | 2 | 14 | 20 |
| Rumex acetosa | 40 | 2 | 41 | 63 |
| Chenopodium album | 63 | 3 | 64 | 75 |
| Taraxacum officinale | 50 | 42 | 71 | 96 |
| Lotus corniculatus | 7 | 0 | 7 | 35 |
| Plantago lanceolata | 50 | 0 | 50 | 60 |
| Festuca ovina | 17 | 0 | 17 | 82 |
| Plantago major | 37 | 0 | 37 | 55 |
| Ranunculus repens | 18 | 80 | 84 | 87 |
| Bellis perennis | 27 | 5 | 31 | 68 |

TABLE 4

Table 4: Herbicide combination according to the invention consisting of herbicidally active fatty acids and thiencarbazone-methyl.

| Weed | Herbicidally active fatty acids 20000 g of active compound/ha; herbicidal effect [%] | Thiencarbazone-methyl 20 g of active compound/ha; herbicidal effect [%] | Herbicidal effect [%] calculated according to Colby | Herbicidal effect [%] found |
|---|---|---|---|---|
| Trifolium repens | 25 | 55 | 66 | 70 |
| Achillea millefolium | 32 | 25 | 49 | 65 |
| Stellaria media | 12 | 53 | 59 | 58 |
| Rumex acetosa | 40 | 52 | 71 | 93 |
| Chenopodium album | 63 | 23 | 72 | 90 |
| Taraxacum officinale | 50 | 38 | 69 | 96 |
| Lotus corniculatus | 7 | 2 | 9 | 63 |
| Plantago lanceolata | 50 | 67 | 84 | 93 |
| Festuca ovina | 17 | 42 | 52 | 88 |
| Plantago major | 37 | 87 | 92 | 95 |
| Ranunculus repens | 18 | 97 | 98 | 93 |
| Bellis perennis | 27 | 28 | 47 | 87 |

TABLE 5

Table 5: Herbicide combination according to the invention consisting of herbicidally active fatty acids and flazasulfuron.

| Weed | Herbicidally active fatty acids 20000 g of active compound/ha; herbicidal effect [%] | Flazasulfuron 37.5 g of active compound/ha; herbicidal effect [%] | Herbicidal effect [%] calculated according to Colby | Herbicidal effect [%] found |
|---|---|---|---|---|
| Trifolium repens | 25 | 63 | 72 | 78 |
| Achillea millefolium | 32 | 67 | 78 | 95 |
| Stellaria media | 12 | 95 | 96 | 98 |
| Rumex acetosa | 40 | 52 | 71 | 95 |
| Chenopodium album | 63 | 70 | 89 | 98 |
| Taraxacum officinale | 50 | 87 | 94 | 100 |
| Lotus corniculatus | 7 | 23 | 28 | 72 |
| Plantago lanceolata | 50 | 7 | 54 | 65 |
| Festuca ovina | 17 | 68 | 73 | 97 |
| Plantago major | 37 | 75 | 84 | 87 |
| Ranunculus repens | 18 | 99 | 99 | 100 |
| Bellis perennis | 27 | 52 | 65 | 87 |

TABLE 6

Table 6: Herbicide combination according to the invention consisting of herbicidally active fatty acids and amidosulfuron.

| Weed | Herbicidally active fatty acids 20000 g of active compound/ha; herbicidal effect [%] | Amidosulfuron 30 g of active compound/ha; herbicidal effect [%] | Herbicidal effect [%] calculated according to Colby | Herbicidal effect [%] found |
|---|---|---|---|---|
| Trifolium repens | 25 | 13 | 35 | 20 |
| Achillea millefolium | 32 | 18 | 44 | 47 |
| Stellaria media | 12 | 10 | 21 | 20 |
| Rumex acetosa | 40 | 28 | 57 | 77 |
| Chenopodium album | 63 | 27 | 73 | 80 |
| Taraxacum officinale | 50 | 88 | 94 | 96 |
| Lotus corniculatus | 7 | 0 | 7 | 13 |
| Plantago lanceolata | 50 | 13 | 57 | 68 |
| Festuca ovina | 17 | 0 | 17 | 17 |
| Plantago major | 37 | 88 | 92 | 88 |
| Ranunculus repens | 18 | 96 | 97 | 92 |
| Bellis perennis | 27 | 33 | 51 | 72 |

TABLE 7

Table 7: Herbicide combination according to the invention consisting of herbicidally active fatty acids and ethoxysulfuron.

| Weed | Herbicidally active fatty acids 20000 g of active compound/ha; herbicidal effect [%] | Ethoxysulfuron 60 g of active compound/ha; herbicidal effect [%] | Herbicidal effect [%] calculated according to Colby | Herbicidal effect [%] found |
|---|---|---|---|---|
| Trifolium repens | 25 | 47 | 60 | 65 |
| Achillea millefolium | 32 | 13 | 41 | 40 |
| Stellaria media | 12 | 5 | 16 | 13 |
| Rumex acetosa | 40 | 25 | 55 | 73 |
| Chenopodium album | 63 | 5 | 65 | 65 |
| Taraxacum officinale | 50 | 38 | 69 | 83 |
| Lotus corniculatus | 7 | 0 | 7 | 10 |
| Plantago lanceolata | 50 | 5 | 53 | 53 |
| Festuca ovina | 17 | 0 | 17 | 13 |
| Plantago major | 37 | 0 | 37 | 62 |
| Ranunculus repens | 18 | 92 | 93 | 93 |
| Bellis perennis | 27 | 10 | 34 | 47 |

TABLE 8

Table 8: Herbicide combination according to the invention consisting of herbicidally active fatty acids and foramsulfuron.

| Weed | Herbicidally active fatty acids 10000 g of active compound/ha; herbicidal effect [%] | Foramsulfuron 60 g of active compound/ha; herbicidal effect [%] | Herbicidal effect [%] calculated according to Colby | Herbicidal effect [%] found |
|---|---|---|---|---|
| *Chenopodium album* | 16.7 | 13.3 | 28 | 96.7 |
| *Festuca ovina* | 0 | 58.3 | 58 | 98 |
| *Plantago major* | 0 | 33.3 | 33 | 51.7 |
| *Taraxacum officinale* | 0 | 75 | 75 | 98 |
| *Poa annua* | 0 | 73.3 | 73 | 95.3 |
| *Trifolium repens* | 0 | 60 | 60 | 76.7 |

TABLE 9

Table 9: Herbicide combination according to the invention consisting of herbicidally active fatty acids and foramsulfuron.

| Weed | Herbicidally active fatty acids 10000 g of active compound/ha; herbicidal effect [%] | Foramsulfuron 15 g of active compound/ha; herbicidal effect [%] | Herbicidal effect [%] calculated according to Colby | Herbicidal effect [%] found |
|---|---|---|---|---|
| *Chenopodium album* | 16.7 | 0 | 17 | 81.7 |
| *Festuca ovina* | 0 | 6.7 | 7 | 95 |
| *Plantago major* | 0 | 0 | 0 | 36.7 |
| *Taraxacum officinale* | 0 | 45 | 45 | 88.3 |
| *Poa annua* | 0 | 18.3 | 18 | 68.3 |
| *Trifolium repens* | 0 | 18.3 | 18 | 36.7 |

TABLE 10

Table 10: Herbicide combination according to the invention consisting of herbicidally active fatty acids and foramsulfuron.

| Weed | Herbicidally active fatty acids 30000 g of active compound/ha; herbicidal effect [%] | Foramsulfuron 60 g of active compound/ha; herbicidal effect [%] | Herbicidal effect [%] calculated according to Colby | Herbicidal effect [%] found |
|---|---|---|---|---|
| *Chenopodium album* | 50 | 13.3 | 57 | 90 |
| *Festuca ovina* | 23.3 | 58.3 | 68 | 98 |
| *Plantago major* | 36.7 | 33.3 | 58 | 50 |
| *Taraxacum officinale* | 48.3 | 75 | 87 | 98.7 |
| *Poa annua* | 0 | 73.3 | 73 | 88.3 |
| *Trifolium repens* | 0 | 60 | 60 | 80 |

TABLE 11

Table 11: Herbicide combination according to the invention consisting of herbicidally active fatty acids and foramsulfuron.

| Weed | Herbicidally active fatty acids 30000 g of active compound/ha; herbicidal effect [%] | Foramsulfuron 15 g of active compound/ha; herbicidal effect [%] | Herbicidal effect [%] calculated according to Colby | Herbicidal effect [%] found |
|---|---|---|---|---|
| *Chenopodium album* | 50 | 0 | 50 | 86.7 |
| *Festuca ovina* | 23.3 | 6.7 | 28 | 86.7 |
| *Plantago major* | 36.7 | 0 | 37 | 38.3 |
| *Taraxacum officinale* | 48.3 | 45 | 72 | 97.3 |
| *Poa annua* | 0 | 18.3 | 18 | 26.7 |
| *Trifolium repens* | 0 | 18.3 | 18 | 33.3 |

TABLE 12

Table 12: Herbicide combination according to the invention consisting of herbicidally active fatty acids and iodosulfuron.

| Weed | Herbicidally active fatty acids 10000 g of active compound/ha; herbicidal effect [%] | Iodosulfuron-methyl sodium salt 10 g of active compound/ha; herbicidal effect [%] | Herbicidal effect [%] calculated according to Colby | Herbicidal effect [%] found |
|---|---|---|---|---|
| *Chenopodium album* | 16.7 | 40 | 50 | 100 |
| *Festuca ovina* | 0 | 6.7 | 7 | 23.3 |
| *Plantago major* | 0 | 53.3 | 53 | 85 |
| *Taraxacum officinale* | 0 | 85 | 85 | 98 |
| *Poa annua* | 0 | 0 | 0 | 0 |
| *Trifolium repens* | 0 | 80 | 80 | 95 |

TABLE 13

Table 13: Herbicide combination according to the invention consisting of herbicidally active fatty acids and iodosulfuron.

| Weed | Herbicidally active fatty acids 10000 g of active compound/ha; herbicidal effect [%] | Iodosulfuron-methyl sodium salt 1 g of active compound/ha; herbicidal effect [%] | Herbicidal effect [%] calculated according to Colby | Herbicidal effect [%] found |
|---|---|---|---|---|
| *Chenopodium album* | 16.7 | 0 | 17 | 70 |
| *Festuca ovina* | 0 | 0 | 0 | 16.7 |
| *Plantago major* | 0 | 0 | 0 | 25 |
| *Taraxacum officinale* | 0 | 18.3 | 18 | 73.3 |
| *Poa annua* | 0 | 0 | 0 | 0 |
| *Trifolium repens* | 0 | 18.3 | 18 | 46.7 |

TABLE 14

Table 14: Herbicide combination according to the invention consisting of herbicidally active fatty acids and iodosulfuron.

| Weed | Herbicidally active fatty acids 30000 g of active compound/ha; herbicidal effect [%] | Iodosulfuron-methyl sodium salt 10 g of active compound/ha; herbicidal effect [%] | Herbicidal effect [%] calculated according to Colby | Herbicidal effect [%] found |
|---|---|---|---|---|
| Chenopodium album | 50 | 40 | 70 | 99 |
| Festuca ovina | 23.3 | 6.7 | 28 | 46.7 |
| Plantago major | 36.7 | 53.3 | 70 | 91.7 |
| Taraxacum officinale | 48.3 | 85 | 92 | 99.3 |
| Poa annua | 0 | 0 | 0 | 0 |
| Trifolium repens | 0 | 80 | 80 | 96.7 |

TABLE 15

Table 15: Herbicide combination according to the invention consisting of herbicidally active fatty acids and iodosulfuron.

| Weed | Herbicidally active fatty acids 30000 g of active compound/ha; herbicidal effect [%] | Iodosulfuron-methyl sodium salt 1 g of active compound/ha; herbicidal effect [%] | Herbicidal effect [%] calculated according to Colby | Herbicidal effect [%] found |
|---|---|---|---|---|
| Chenopodium album | 50 | 0 | 50 | 81.7 |
| Festuca ovina | 23.3 | 0 | 23 | 36.7 |
| Plantago major | 36.7 | 0 | 37 | 36.7 |
| Taraxacum officinale | 48.3 | 18.3 | 58 | 83.3 |
| Poa annua | 0 | 0 | 0 | 0 |
| Trifolium repens | 0 | 18.3 | 18 | 43.3 |

TABLE 16

Table 16: Herbicide combination according to the invention consisting of herbicidally active fatty acids and also foramsulfuron and iodosulfuron.

| Weed | Herbicidally active fatty acids 10000 g of active compound/ha; herbicidal effect [%] | Foramsulfuron 60 g of active compound/ha; herbicidal effect [%] | Iodosulfuron-methyl sodium salt 10 g of active compound/ha; herbicidal effect [%] | Herbicidal effect [%] calculated according to Colby | Herbicidal effect [%] found |
|---|---|---|---|---|---|
| Chenopodium album | 16.7 | 13.3 | 40 | 57 | 100 |
| Festuca ovina | 0 | 58.3 | 6.7 | 61 | 98 |
| Plantago major | 0 | 33.3 | 53.3 | 69 | 96.7 |
| Taraxacum officinale | 0 | 75 | 85 | 96 | 99.3 |
| Poa annua | 0 | 73.3 | 0 | 73 | 98.7 |
| Trifolium repens | 0 | 60 | 80 | 92 | 98.7 |

TABLE 17

Table 17: Herbicide combination according to the invention consisting of herbicidally active fatty acids and also foramsulfuron and iodosulfuron.

| Weed | Herbicidally active fatty acids 10000 g of active compound/ha; herbicidal effect [%] | Foramsulfuron 15 g of active compound/ha; herbicidal effect [%] | Iodosulfuron-methyl sodium salt 1 g of active compound/ha; herbicidal effect [%] | Herbicidal effect [%] calculated according to Colby | Herbicidal effect [%] found |
|---|---|---|---|---|---|
| Chenopodium album | 16.7 | 0 | 0 | 17 | 86.7 |
| Festuca ovina | 0 | 6.7 | 0 | 7 | 91.7 |
| Plantago major | 0 | 0 | 0 | 0 | 53.3 |
| Taraxacum officinale | 0 | 45 | 18.3 | 55 | 95 |
| Poa annua | 0 | 18.3 | 0 | 18 | 73.3 |
| Trifolium repens | 0 | 18.3 | 18.3 | 33 | 73.3 |

TABLE 18

Table 18: Herbicide combination according to the invention consisting of herbicidally active fatty acids and also foramsulfuron and iodosulfuron.

| Weed | Herbicidally active fatty acids 10000 g of active compound/ha; herbicidal effect [%] | Foramsulfuron 15 g of active compound/ha; herbicidal effect [%] | Iodosulfuron-methyl sodium salt 10 g of active compound/ha; herbicidal effect [%] | Herbicidal effect [%] calculated according to Colby | Herbicidal effect [%] found |
|---|---|---|---|---|---|
| Chenopodium album | 16.7 | 0 | 40 | 50 | 98.3 |
| Festuca ovina | 0 | 6.7 | 6.7 | 13 | 94 |
| Plantago major | 0 | 0 | 53.3 | 53 | 90.7 |
| Taraxacum officinale | 0 | 45 | 85 | 92 | 98 |
| Poa annua | 0 | 18.3 | 0 | 18 | 90 |
| Trifolium repens | 0 | 18.3 | 80 | 84 | 98.7 |

TABLE 19

Table 19: Herbicide combination according to the invention consisting of herbicidally active fatty acids and also foramsulfuron and iodosulfuron.

| Weed | Herbicidally active fatty acids 10000 g of active compound/ha; herbicidal effect [%] | Foramsulfuron 60 g of active compound/ha; herbicidal effect [%] | Iodosulfuron-methyl sodium salt 1 g of active compound/ha; herbicidal effect [%] | Herbicidal effect [%] calculated according to Colby | Herbicidal effect [%] found |
|---|---|---|---|---|---|
| Chenopodium album | 16.7 | 13.3 | 0 | 28 | 91.7 |
| Festuca ovina | 0 | 58.3 | 0 | 58 | 98 |
| Plantago major | 0 | 33.3 | 0 | 33 | 55 |
| Taraxacum officinale | 0 | 75 | 18.3 | 80 | 98 |
| Poa annua | 0 | 73.3 | 0 | 73 | 99 |
| Trifolium repens | 0 | 60 | 18.3 | 67 | 86.7 |

TABLE 20

Table 20: Herbicide combination according to the invention consisting of herbicidally active fatty acids and also foramsulfuron and iodosulfuron.

| Weed | Herbicidally active fatty acids 20000 g of active compound/ha; herbicidal effect [%] | Foramsulfuron 45 g of active compound/ha; herbicidal effect [%] | Iodosulfuron-methyl sodium salt 1.25 g of active compound/ha; herbicidal effect [%] | Herbicidal effect [%] calculated according to Colby | Herbicidal effect [%] found |
|---|---|---|---|---|---|
| Chenopodium album | 48 | 13 | 0 | 55 | 92 |
| Festuca ovina | 13 | 53 | 0 | 60 | 98 |
| Plantago major | 17 | 23 | 3 | 38 | 62 |
| Taraxacum officinale | 30 | 70 | 18 | 83 | 100 |
| Poa annua | 0 | 48 | 0 | 48 | 90 |
| Trifolium repens | 0 | 53 | 32 | 68 | 85 |

TABLE 21

Table 21: Herbicide combination according to the invention consisting of herbicidally active fatty acids and also foramsulfuron and iodosulfuron.

| Weed | Herbicidally active fatty acids 20000 g of active compound/ha; herbicidal effect [%] | Foramsulfuron 60 g of active compound/ha; herbicidal effect [%] | Iodosulfuron-methyl sodium salt 2.5 g of active compound/ha; herbicidal effect [%] | Herbicidal effect [%] calculated according to Colby | Herbicidal effect [%] found |
|---|---|---|---|---|---|
| Chenopodium album | 48 | 13 | 10 | 60 | 98 |
| Festuca ovina | 13 | 58 | 0 | 64 | 98 |
| Plantago major | 17 | 33 | 30 | 61 | 68 |
| Taraxacum officinale | 30 | 75 | 42 | 90 | 99 |
| Poa annua | 0 | 73 | 0 | 73 | 94 |
| Trifolium repens | 0 | 60 | 45 | 78 | 87 |

TABLE 22

Table 22: Herbicide combination according to the invention consisting of herbicidally active fatty acids and also foramsulfuron and iodosulfuron.

| Weed | Herbicidally active fatty acids 30000 g of active compound/ha; herbicidal effect [%] | Foramsulfuron 60 g of active compound/ha; herbicidal effect [%] | Iodosulfuron-methyl sodium salt 10 g of active compound/ha; herbicidal effect [%] | Herbicidal effect [%] calculated according to Colby | Herbicidal effect [%] found |
|---|---|---|---|---|---|
| Chenopodium album | 50 | 13.3 | 40 | 74 | 100 |
| Festuca ovina | 23.3 | 58.3 | 6.7 | 70 | 99.3 |
| Plantago major | 36.7 | 33.3 | 53.3 | 80 | 90.7 |
| Taraxacum officinale | 48.3 | 75 | 85 | 98 | 100 |
| Poa annua | 0 | 73.3 | 0 | 73 | 90 |
| Trifolium repens | 0 | 60 | 80 | 92 | 96 |

TABLE 23

Table 23: Herbicide combination according to the invention consisting of herbicidally active fatty acids and also foramsulfuron and iodosulfuron.

| Weed | Herbicidally active fatty acids 30000 g of active compound/ha; herbicidal effect [%] | Foramsulfuron 15 g of active compound/ha; herbicidal effect [%] | Iodosulfuron-methyl sodium salt 1 g of active compound/ha; herbicidal effect [%] | Herbicidal effect [%] calculated according to Colby | Herbicidal effect [%] found |
|---|---|---|---|---|---|
| Chenopodium album | 50 | 0 | 0 | 50 | 91 |
| Festuca ovina | 23.3 | 6.7 | 0 | 28 | 90 |
| Plantago major | 36.7 | 0 | 0 | 37 | 45 |
| Taraxacum officinale | 48.3 | 45 | 18.3 | 77 | 96 |
| Poa annua | 0 | 18.3 | 0 | 18 | 45 |
| Trifolium repens | 0 | 18.3 | 18.3 | 33 | 68.3 |

TABLE 24

Table 24: Herbicide combination according to the invention consisting of herbicidally active fatty acids and also foramsulfuron and iodosulfuron.

| Weed | Herbicidally active fatty acids 30000 g of active compound/ha; herbicidal effect [%] | Foramsulfuron 15 g of active compound/ha; herbicidal effect [%] | Iodosulfuron-methyl sodium salt 10 g of active compound/ha; herbicidal effect [%] | Herbicidal effect [%] calculated according to Colby | Herbicidal effect [%] found |
|---|---|---|---|---|---|
| Chenopodium album | 50 | 0 | 40 | 70 | 99 |
| Festuca ovina | 23.3 | 6.7 | 6.7 | 33 | 98 |
| Plantago major | 36.7 | 0 | 53.3 | 70 | 90 |
| Taraxacum officinale | 48.3 | 45 | 85 | 96 | 99.3 |
| Poa annua | 0 | 18.3 | 0 | 18 | 71.7 |
| Trifolium repens | 0 | 18.3 | 80 | 84 | 96 |

TABLE 25

Table 25: Herbicide combination according to the invention consisting of herbicidally active fatty acids and also foramsulfuron and iodosulfuron.

| Weed | Herbicidally active fatty acids 30000 g of active compound/ha; herbicidal effect [%] | Foramsulfuron 60 g of active compound/ha; herbicidal effect [%] | Iodosulfuron-methyl sodium salt 1 g of active compound/ha; herbicidal effect [%] | Herbicidal effect [%] calculated according to Colby | Herbicidal effect [%] found |
|---|---|---|---|---|---|
| Chenopodium album | 50 | 13.3 | 0 | 57 | 99 |
| Festuca ovina | 23.3 | 58.3 | 0 | 68 | 98.7 |
| Plantago major | 36.7 | 33.3 | 0 | 58 | 75 |
| Taraxacum officinale | 48.3 | 75 | 18.3 | 89 | 98.7 |
| Poa annua | 0 | 73.3 | 0 | 73 | 88.3 |
| Trifolium repens | 0 | 60 | 18.3 | 67 | 81.7 |

The invention claimed is:

1. A herbicide composition comprising as component (A) at least two herbicidally active α-monocarboxyl fatty acids which, independently of one another contain hydrocarbon chains of 8 to 10 carbon atoms and are present in a ratio of between 65:35 to 40:60, wherein the α-monocarboxyl fatty acids are selected from the group consisting of caprylic acid, pelargonic acid, and capric acid; and as component (B) at least one ALS inhibitor selected from the group consisting of iodosulfuron-methyl, foramsulfuron, mesosulfuron-methyl, flazasulfuron and thiencarbazone-methyl, wherein the weight ratio of components (A) and (B) is in the range of from 30,000:1 to 167:1; and wherein (A) and (B) are present in amounts effective to provide synergistic activity.

2. The herbicide composition as claimed in claim 1 where the component (B) used is foramsulfuron and the weight ratio of components (A) and (B) is in a range of from 2000:1 to 167:1 or the component (B) used is iodosulfuron-methyl and the weight ratio of components (A) and (B) is in a range of from 30000:1 to 1000:1 or the component (B) used is mesosulfuron-methyl and the weight ratio of components (A) and (B) is in a range of from 4000:1 to 333:1 or the component (B) used is thiencarbazone-methyl and the weight ratio of components (A) and (B) is in a range of from 3000:1 to 333:1 or the component (B) used is flazasulfuron and the weight ratio of components (A) and (B) is in a range of from 3000:1 to 200:1.

3. The herbicide composition as claimed in claim 1 where, in addition to component (A), at least two different ALS inhibitors are used as component (B).

4. The herbicide composition as claimed in claim 3 where the two different ALS inhibitors are iodosulfuron-methyl and foramsulfuron.

5. The herbicide composition as claimed in claim 4 where 15-60 parts by weight of foramsulfuron and 2500-30000 parts by weight of component (A) are present per part by weight of iodosulfuron-methyl.

6. The herbicide composition as claimed in claim 1, comprising an effective amount of components (A) and (B) and additionally one or more further components from the group of agrochemically active compounds of a different type, formulation auxiliaries and additives customary in crop protection.

7. The herbicide composition as claimed in claim 1, where the component (B) used is foramsulfuron-methyl and the weight ratio of components (A) and (B) is in a range of from 2000:1 to 167:1.

8. The herbicide composition as claimed in claim 1, where the component (B) used is iodosulfuron-methyl and the weight ratio of components (A) and (B) is in a range of from 30000:1 to 1000:1.

9. The herbicide composition as claimed in claim 1, where the component (B) used is mesosulfuron-methyl and the weight ratio of components (A) and (B) is in a range of from 4000:1 to 333:1.

10. The herbicide composition as claimed in claim 1, where the component (B) used is thiencarbazone-methyl and the weight ratio of components (A) and (B) is in a range of from 3000:1 to 333:1.

11. The herbicide composition as claimed in claim 1, where the component (B) used is flazasulfuron and the weight ratio of components (A) and (B) is in a range of from 3000:1 to 200:1.

12. A method for controlling weeds, comprising applying a herbicide composition as claimed in claim 1 to the weeds and/or a habitat thereof.

13. The method for controlling weeds as claimed in claim 12 wherein component (A) and component (B) of the herbicide composition are mixed only shortly before application to the weeds and/or habitat.

* * * * *